United States Patent [19]
Scher et al.

[11] Patent Number: 5,049,182

[45] Date of Patent: Sep. 17, 1991

[54] SINGLE-PACKAGE AGRICULTURAL FORMULATIONS COMBINING IMMEDIATE AND TIME-DELAYED DELIVERY

[75] Inventors: Herbert B. Scher, Moraga; Marius Rodson, El Cerrito, both of Calif.; Jose L. Calvo, Finchampstead; Miguel Gimeno, Bracknell, both of England

[73] Assignee: ICI Americas Inc., Wilmington, Del.

[21] Appl. No.: 291,723

[22] Filed: Feb. 3, 1989

[51] Int. Cl.$^5$ .............................................. A01N 25/28
[52] U.S. Cl. .......................................... 71/93; 71/88; 71/3; 71/100; 71/DIG. 1; 71/118; 71/121; 424/489; 424/419; 424/497; 428/402; 428/402.2; 428/402.24
[58] Field of Search ................ 71/DIG. 1, 93, 3, 88, 71/121, 100, 118; 424/489, 497, 419; 428/402, 402.2, 402.24

[56] References Cited

U.S. PATENT DOCUMENTS

| | | | |
|---|---|---|---|
| 3,577,515 | 5/1971 | Vandegaer | 424/497 |
| 4,046,741 | 9/1977 | Scher | 260/77.5 A |
| 4,140,516 | 2/1979 | Scher . | |
| 4,266,965 | 5/1981 | Simons | 71/118 |
| 4,285,720 | 8/1981 | Scher . | |
| 4,360,376 | 11/1982 | Koestler | 71/121 |
| 4,439,488 | 3/1984 | Trimnell et al. | 71/DIG. 1 |
| 4,456,569 | 6/1984 | Rodson et al. | 525/58 |
| 4,534,783 | 8/1985 | Beestman . | |
| 4,640,709 | 2/1987 | Beestman | 71/93 |
| 4,643,764 | 2/1987 | Scher . | |
| 4,657,582 | 4/1987 | Huber | 71/121 |
| 4,677,003 | 6/1987 | Redlich et al. | 428/402.24 |

*Primary Examiner*—Lester L. Lee
*Assistant Examiner*—E. J. Kraus
*Attorney, Agent, or Firm*—Lynn Marcus-Wyner; Denis A. Polyn

[57] ABSTRACT

Microcapsule formulations are combined with emulsions or particle dispersions in a single-package formulation which is storage-stable and provides substantially the full efficacy of each of the two forms as if applied individually. The single-package formulation is suspension having two dispersed phases—the first being an active species encapsulated in a shell of inert polymeric diffusion-limiting material (i.e., a microcapsule), and the second being an active species in water-insoluble form with no diffusion-limiting barrier at its surface. An appropriate suspension system is included to prevent the dispersed phases from agglomerating within themselves and with each other. The invention is useful in combining two different active ingredients as well as in combining immediate-delivery and delayed-delivery forms of the same active ingredient. The invention may for example involve combining a biocide with an activity modifier such as a safener, with the effect of lowering the needed amount of one or the other by removing it to a separate phase. In certain cases, a unique combination of surface-active agents maintains the phases in suspension.

8 Claims, No Drawings

SINGLE-PACKAGE AGRICULTURAL FORMULATIONS COMBINING IMMEDIATE AND TIME-DELAYED DELIVERY

BACKGROUND OF THE INVENTION

This invention relates to formulations of biologically active agents suitable for agricultural field application.

Agricultural chemicals, particularly herbicides, are sold in a wide variety of formulations, including solid formulations such as powders, dusts, granules and timerelease microcapsules, liquid formulations such as solutions and emulsions, and suspensions of solids in liquid carriers. The choice of the formulation is generally governed by such considerations as the physical characteristics of the active ingredient, the type of crop or weed species to which the formulation is to be applied and its growth cycle, and the timing of the application (postemergence or preemergence).

Delayed-release formulations are favored for their ability to provide herbicidal efficacy over an extended period of time. Initial activity is often low, however, while the concentration of active ingredient in the soil slowly rises to an effective level. In many cases, delayed-release formulations must be supplemented with a formulation providing immediate delivery of the same active ingredient to both avoid the initial weed growth and provide continuous control over the crop's growth cycle. The conventional solution is a two-package formulation in which the delayed-release and immediate delivery formulations are kept apart until field application.

In many cases, two different active ingredients are needed at the same time for effective weed control. The combination of two active ingredients in a single formulation, however, is not readily achieved in many cases. Difficulties such as chemical or physical incompatibility of the active species, and the need for special formulating techniques for certain species due to low melting points or other characteristics frequently make it impractical or unfeasible to combine the two species in a single-package formulation.

Adding further to these difficulties is the need to maintain the physical stability of the formulation during storage. This is often critical to its effectiveness when finally applied to a field for crop protection. This is of particular concern with regard to multi-phase systems such as suspensions and emulsions. Immediate delivery systems such as emulsions, emulsifiable concentrates and suspensions of solid particles can undergo transformations such as changes in phase, particle settling and particle or droplet agglomeration. Such transformations are often detrimental to the dispersibility of the active ingredient in the field, and sometimes even to the ability of the formulation to deliver the active ingredient to the soil or plant surface to which the formulation is applied. Furthermore, such transformations are difficult if not impossible to reverse.

In the case of water-suspended time-release microcapsules, it is essential that the active ingredient remain in the microcapsule until field application. Since the encapsulated phase is generally a solution of the active ingredient in a non-water-miscible solvent, the surrounding water serves as a barrier preventing rapid outward diffusion of the active ingredient. When the solvent is a volatile solvent, the water also serves to prevent evaporation of the solvent and any solidification of the active ingredient which might occur as a result.

The placement of an additional dispersed phase, whether solid or liquid, in the water presents a risk of upsetting the stability of a multi-phase formulation. Adding solid particles or suspended droplets to a microcapsule suspension should be particularly hazardous to the suspension stability of the entire system, since the surface of the microcapsule is chemically distinct from that of the added material. The microcapsule generally has a microporous polymer shell whose surface charges and accessible functional groups will differ considerably from those of the active ingredient which is present on the droplet or particle surface. The introduction of the droplet or particle may thus upset the balance of surface forces set up by the suspension agents normally used for the microcapsules and interfere with their effectiveness.

In addition to maintaining the microcapsule dispersion, the system must hold the added phase in a dispersed state as well, and also maintain the water barrier around the microcapsules. Thus, each dispersed phase must be prevented from agglomerating with itself as well as with the other dispersed phase. In view of the surface differences between the two dispersed phases, it is not likely that a single suspension system would be readily found which would serve all these functions.

When the material added to the microcapsule suspension are droplets forming an emulsion, it is often critical that the active ingredient in the emulsion not crystallize during storage. For active ingredients with low water solubility, crystallization is avoided by careful maintenance of the equilibrium distribution of the active between the droplets and the water, and control of the diffusion of the active across the phase boundary, which involves careful control of the proportion of solvent to active ingredient in the droplets. The introduction of active ingredient to the continuous phase from a second source (i.e., diffusing out of the microcapsule) runs the risk of causing active ingredient to crystallize out of the continuous phase due to an abnormally high concentration.

SUMMARY OF THE INVENTION

It has now been discovered that microcapsule formulations can indeed be combined with emulsions or particle dispersions in a single-package formulation which is storage-stable and hence provides substantially the full biocidal efficacy of each of the two forms as if they were applied individually. The single-package formulation is thus a suspension having two dispersed phases—the first being a biologically active agent encapsulated in a shell of inert polymeric diffusion-limiting material (i.e., a microcapsule) providing a time-delayed gradual release of the agent through the shell walls, and the second being a biologically active agent in water-insoluble form with no diffusion-limiting barrier at its surface—together with an appropriate suspension system to prevent the dispersed phases from agglomerating within themselves and with each other. The second dispersed phase may be either droplets of a water-immiscible active ingredient or solution, or solid active ingredient particles. The invention is useful in combining two different active ingredients as well as in combining immediate-delivery and delayed-delivery forms of the same ingredient. The invention is also useful in combining a biocide with an activity modifier such as a safener, with the effect of lowering the needed amount of one or the other by removing it to a separate phase. In certain cases, a unique combination of surface-active agents has also been discovered which maintains the phases in suspension.

The invention is of particular utility in herbicide formulations, notably with herbicides such as thiocarbamates, triazines, amides and dinitroanilines. Further embodiments, objects and advantages of the invention will be apparent from the description which follows.

DETAILED DESCRIPTION OF THE INVENTION AND PREFERRED EMBODIMENTS

The present invention is applicable to microcapsule structures in general, and extends to the wide range of microcapsule technology described in the patent literature and in commercial use. Descriptions of various types of microcapsules and various methods for forming microcapsules may be found for example, in Vandegaer, U.S. Pat. No. 3,577,515 (May 4, 1971); Scher, U.S. Pat. No. 4,046,741 (Sept. 6, 1977); Scher, U.S. Pat. No. 4,140,516 (Feb. 20, 1979); Scher. U.S. Pat. No. 4,285,720 (Aug. 21, 1981): and Scher, U.S. Pat. No. 4,643,764 (Feb. 17, 1987). The disclosures of these patents are incorporated herein by reference. Microcapsules formed by interfacial polycondensation are preferred, with sizes preferably ranging from about 1 micron to about 100 microns in diameter. Such microcapsules have porous shells of inert polymeric material which maintains its integrity during storage and application, and delivers the active ingredient by slow diffusion from the capsule interior through the shell to the locus of application. Preferred polymers are polyureas.

The contents of the microcapsule are generally liquid, and are comprised of either a liquid active ingredient (or combination of active ingredients) which is non-water-miscible, or an active ingredient dissolved in a water-immiscible solvent. The art extends to a wide range of such solvents, examples of which are aromatics such as xylene and benzene, aliphatics such as pentane and hexane, and others such as carbon disulfide and carbon tetrachloride.

The free active ingredient, i.e., the ingredient included outside the microcapsules and intended for immediate release to the locus of application, may be either solid particles or water-immiscible liquid droplets suspended in the aqueous phase together with the microcapsules.

When solid particles are used, they may be equivalent in size and composition to such known formulations as wettable powders or presuspended solids. They are generally finely divided particles in which the solid active ingredient is either the entire particle or is retained in a solid matrix, either by retention inside the pores thereof or as a coating on the surface. Examples of solid matrices suitable for this purpose include fuller's earth, kaolin clays, attapulgite clays, silicas and other organic or inorganic water-immiscible solids. The content of active ingredient retained in these matrices may range from 5% to 95%. The size of these particles may vary widely, but will generally fall within the range of about 0.5 microns to about 100 microns. Generally, any ratio of the ingredients will work. In preferred embodiments for such systems, the microcapsules will comprise from about 5% to about 50% of the formulation, and the particles will comprise from about 5% to about 50%, all by weight.

When water-immiscible droplets are used, they may be equivalent in size and composition to emulsions typically used in field application. They may consist either of the active ingredient itself, provided it is a water-immiscible liquid at storage and application temperatures, or the active ingredient dissolved in a water-immiscible solvent. The art extends to many such solvents, for example xylene, heavy aromatic naphthas, and isophorone. The concentration of active ingredient in such a solution may range from 0.5% to 95% by weight. The droplets are formed by high shear agitation and maintained by the suspension system as a whole. While the actual droplet size may vary widely, it will generally lie within the range of about 0.5 microns to about 100 microns. In preferred embodiments for such systems, the microcapsules will comprise from about 5% to about 50% of the formulation and the droplets will comprise from about 5% to about 50%, all by weight.

The suspension system will generally be a combination of agents such as surfactants, clays, polymers and other suspension stabilizing materials appropriately selected to keep both the microcapsules and the free active ingredient phase in suspension and to avoid agglomeration among each dispersed phase as well as between the two dispersed phases. A wide range of such agents may be used, and the optimum combination for each particular system of active ingredients will vary. For thiocarbamate herbicides, the preferred suspension systems will contain a xanthan gum, an attapulgite clay, and sodium tripolyphosphate. For example, for systems in which the active ingredient in both the microcapsules and the free dispersed phase is a combination of S-ethyl cyclohexylethylthiocarbamate and the safener N,N-diallyl-1.1-dichloroacetamide, a favored suspension system is the combination of a xanthan gum, preferably at about 0.01% to about 0.1%, weight, an attapulgite clay, preferably at about 0.1% to about 1.0%, aluminum sulfate, preferably at about 0.01% to about 0.1%, and sodium tripolyphosphate. preferably at about 0.003% to about 0.1%, all by weight. As a further example, for systems in which the active ingredient in both the microcapsules and the free dispersed phase is a combination of S-ethyl di-n-propylthiocarbamate and the safener N,N-diallyl-1,1-dichloroacetamide a favored suspension system is the combination of a xanthan gum, preferably at about 0.01% to about 0.1%. weight, an attapulgite clay. preferably at about 0.1% to about 1.0%, and sodium tripolyphosphate, preferably at about 0.01% to about 0.1%, all by weight. As a still further example, for systems in which the microencapsulated ingredient is a combination of S-ethyl diisobutylthiocarbamate and the safener N,N-diallyl-1,1-dichloroacetamide, and the free active ingredient is solid particles of 2-chloro-4-ethylamino-6-isopropylamino-S-triazine, a favored suspension system is the combination of a xanthan gum, preferably at about 0.01% to about 0.1%, aluminum sulfate, preferably at about 0.01% to about 0.1%, and sodium tripolyphosphate preferably at about 0.01% to about 0.1%, all by weight. A still further example is one in which the microencapsulated active ingredient is α,α,α-trifluoro-2,6-dinitro-N,N-dipropyl-p-toluidine, and the free active ingredient is solid particles of 2-(α-naphthoxy)-N,N-diethylpropionamide. An appropriate suspension system may be a combination of a polyalkylene glycol ether, an ethoxylated alkylaryl ether, an ethoxylated polyarylphenol phosphate, a cresol formaldehyde, a xanthan gum and an attapulgite clay.

The formulations will frequently include additional adjuvants, mostly in very small amounts in proportion to the active ingredients, to serve a variety of functions, mostly associated with the individual active ingredients. These adjuvants may include emulsifiers for those systems in which the free active ingredient forms an emulsion, freezing point depressants, wetting agents, pH modifiers, and biocidal species included to protect some of the other species in the formulation from organisms present in the water during storage. Examples of emulsifiers are anionic and nonionic species, and blends of both types. A typical blend is a combination of nonylphenol ethoxylates and calcium dodecyl benzene sulfonate. An example of a wetting agent is a dialkyl naphthalene sulfonate. An example of a pH modifier is sodium carbonate. An example of a biocidal species is sorbic acid. Other adjuvants will be readily apparent to those skilled in the art.

The formulations of the present invention are prepared according to conventional techniques. In general, the prepared microcapsules in the form of an aqueous dispersion is combined with the other ingredients, including water, and blended under medium to high shear. High shear is particularly preferred when the free active ingredient is in a non-water-miscible liquid phase.

The active ingredients used in either the microcapsule or free phase may be any of a wide variety of biologically active species. Examples are herbicides, insecticides, algicides, fungicides, bactericides, safeners (e.g., antidotes for particular crops), juvenile hormones, and plant growth regulators.

The formulations of the present invention may be applied to the field in any conventional manner. The formulations are aqueous suspensions, but will frequently be further diluted with water before they are applied to the field. The appropriate dilutions as well as the appropriate timing and method of application in each case will be readily apparent to those skilled in the art.

The following examples are offered strictly for illustration and are intended neither to define nor to limit the invention in any manner.

EXAMPLE 1

A formulation of the herbicide Ro-Neet (cycloate) with the safener R-25788, combining suspended microcapsules and an emulsion, was prepared using the following ingredients:

|  | parts by weight |
|---|---|
| S-ethyl cyclohexylethylthiocarbamate (99.3%) | 160.02 |
| N,N-diallyl-2,2-dichloroacetamide (95%) | 13.94 |
| Sponto 221 - blend of nonylphenol ethoxylates and calcium dodecyl benzene sulfonate, supplied by Witco Chemical Corp., Houston, Texas | 7.57 |
| water | 157.92 |
| Kelzan - xanthan gum, supplied by Kelco, San Diego, California | 0.23 |
| sorbic acid | 0.40 |
| sodium tripolyphosphate | 0.12 |
| Attagel 40 - an attapulgite clay, supplied by Engelhard Minerals and Chemicals, Menlo Park, New Jersey | 1.90 |
| aluminum sulfate (27.5% aqueous solution) | 0.23 |
| ethylene glycol | 40.43 |
| flowable microcapsule formulation containing 41.1% S-ethyl cyclohexylethylthiocarbamate | 382.73 |
| and 3.4% N,N-diallyl-2,2-dichloroacetamide (by weight) in polyurea microcapsules of 14.3μ (average) diameter, the microcapsule wall constituting 4.1% by weight of the formulation | |
| Total | 765.49 |

The formulation was prepared by combining the Kelzan, sorbic acid, sodium tripolyphosphate and water with high shear stirring for fifteen minutes. The aluminum sulfate solution and ethylene glycol were then added. After stirring for a few minutes the microcapsule flowable formulation was added. After five additional minutes of stirring, the S-ethyl cyclohexylethylthiocarbamate N,N-diallyl2,2-dichloroacetamide, and the Sponto 221 were combined and added. Stirring was continued for an additional five minutes and pH was adjusted to 11.0 with 50% aqueous caustic. The resulting formulation was a stable suspension of the microcapsules and discrete droplets, both containing the herbicide and safener, the droplets being approximately 5-20 μ in diameter, with no noticeable agglomeration.

EXAMPLE 2

A formulation of the herbicide Eradicane (EPTC plus the safener R-25788), combining suspended microcapsules and an emulsion, was prepared using the following ingredients:

|  | parts by weight |
|---|---|
| S-ethyl dipropylthiocarbamate (98.5% purity) | 347.53 |
| N,N-diallyl-2,2-dichloroacetamide (95%) | 28.96 |
| Sponto 221 ER - blend of nonylphenol ethoxylates and calcium dodecyl benzene sulfonate, supplied by Witco Chemical Corp., Houston, Texas | 7.53 |
| water | 287.30 |
| Kelzan | 0.40 |
| sorbic acid | 1.36 |
| Attagel 40 | 5.1 |
| sodium tripolyphosphate | 0.41 |
| flowable microcapsule formulation containing 37.1% S-ethyl dipropylthiocarbamate, 3.1% N,N-diallyl-2,2-dichloroacetamide and 10.5% xylene (by weight) in polyurea microcapsules of 16μ (average) diameter, the microcapsule wall constituting 4.1% by weight of the formulation | 678.60 |
| Total | 1357.19 |

The formulation was prepared by combining the Kelzan, sorbic acid, Attagel 40, sodium tripolyphosphate and water with high-shear stirring for fifteen minutes. The S-ethyl dipropylthiocarbamate, N,N-diallyl-2,2-dichloroacetamide and Sponto 221 ER were then combined and added to the stirring mixture. After five minutes of additional stirring, the microcapsule flowable formulation was added. Stirring was continued for an additional five minutes and the pH was adjusted to 11.0 with 50% aqueous caustic. The resulting formulation was a stable suspension of the microcapsules and discrete droplets, both containing the herbicide and safener, the droplets being approximately 5-20 μ in diameter, with no noticeable agglomeration.

EXAMPLE 3

A formulation combining the herbicides Sutan+ (butylate plus the safener R-25788) and atrazine, the former as suspended microcapsules and the latter as suspended solid particles, was prepared using the following ingredients:

|  | parts by weight |
|---|---|
| flowable microcapsule formulation containing 48.0% S-ethyl diisobutylthiocarbamate and 2.0% N,N-diallyl-2,2-dichloroacetamide (by weight) in polyurea microcapsules of 10.5µ (average) diameter microcapsules, the microcapsule wall constituting 4.1% by weight of the formulation | 150.0 |
| 2-chloro-4-ethylamino-6-isopropylamino-S-triazine, an air-milled powder of 1-10µ particle diameter, 95% active ingredient | 19.3 |
| Petro BAF - dialkyl naphthalene sulfonate, supplied by Petrochemical Company, Inc., Fort Worth, Texas | 2.5 |
| sorbic acid | 0.21 |
| Kelzan | 0.13 |
| sodium tripolyphosphate | 0.06 |
| sodium carbonate | 1.12 |
| aluminum sulfate (27.5% aqueous solution) | 0.11 |
| Total | 209.43 |

The Petro BAF was dissolved in the water, and the 2-chloro-4-ethylamino-6-isopropylamino-S-triazine was stirred in to form a slurry. The microcapsule flowable was then added and the combination was stirred for twenty minutes with a medium-shear stirrer. The Kelzan, sodium tripolyphosphate, sorbic acid and sodium carbonate were then added and stirring was continued for an additional twenty minutes. The pH was then adjusted to 11.0 with 50% aqueous caustic. The resulting formulation was a stable suspension of the microcapsules and the atrazine particles, with no noticeable agglomeration.

EXAMPLE 4

This is a further illustration of the preparation of a formulation containing Sutan+ microcapsules and atrazine particles in an aqueous suspension. The ingredients were as follows:

|  | parts by weight |
|---|---|
| flowable microcapsule formulation containing 48.0% S-ethyl diisobutylthiocarbamate and 2.0% N,N-diallyl-2,2-dichloroacetamide (by weight) in polyurea microcapsules of 11.5µ (average) diameter, the microcapsule wall constituting 4.1% of the formulation | 3000.0 |
| Petro BAF | 100.0 |
| water | 520.0 |
| 2-chloro-4-ethylamino-6-isopropylamino-S-triazine, an air-milled powder of 1-10µ particle diameter, 95% active ingredient | 386.0 |
| Kelzan | 2.0 |
| Attagel 40 | 7.0 |
| sorbic acid | 3.4 |
| sodium carbonate | 18.4 |
| aluminum sulfate (27.5% aqueous solution) | 2.0 |
| Total | 4038.8 |

All ingredients except the sodium carbonate and the aluminum sulfate were combined and stirred for fifteen minutes with a 2-inch Cowles disperser at 300 rpm. The pH was then raised to 9.0 with 50% aqueous caustic, and the sodium carbonate and aluminum sulfate were added. Stirring was continued for an additional fifteen minutes, and the pH was raised to 11.0. The resulting formulation was a stable suspension of the microcapsules and the atrazine particles, with no noticeable agglomeration.

EXAMPLE 5

This example illustrates the combination of Devrinol (napropamide, or 2-(α-naphthoxy)-N,N-diethylpropionamide) and Treflan (trifluralin, or α,α,α-trifluoro-2,6-dinitro-N,N-dipropyl-p-toluidine). using a particle suspension and a microcapsule suspension.

A Devrinol suspension concentrate was prepared by combining the following ingredients:

|  | parts by weight |
|---|---|
| technical 2-(α-naphthoxy)-N,N-diethyl propionamide | 45.0 |
| blend of polyalkylene glycol ether with ethoxylated alkylaryl ether | 0.5 |
| mixture of water, ethylene glycol and propylene glycol (17.5:3:1) | 43.5 |
| ethoxylated polyarylphenol phosphate (surfactant) | 4.0 |
| cresol formaldehyde dispersant | 1.0 |
| Total | 94.0 |

Small amounts of a silicone defoamer were added during stirring to control foam formation. The mixture was cooled to about 5° C. and milled in a refrigerated bead mill to a particle size of about 5 µ average. A small amount of xanthan gum was then added to prevent sedimentation during a two-year shelf life. Make-up water was added to adjust the active ingredient loading to 450 grams per liter.

A trifluralin microcapsule suspension was prepared with the following contents:

|  | parts by weight |
|---|---|
| α,α,α-trifluoro-2,6-dinitro-N,N-dipropyl-p-toluidine | 35.5 |
| SURE SOL 190 (heavy aromatic solvent naphtha, supplied by Koch Chemical Co.) | 12.5 |
| polyurea capsule wall | 4.0 |
| water and other inerts | balance |
| Total | 100.0 |

The Devrinol suspension concentrate (39.8 parts by weight) was combined with the trifluralin capsule suspension (59.7 parts by weight), and the two were blended together using a low shear stirrer. Xanthan gum (0.05%) and Attagel 40 (0.5%) were added to obtain a structure that will prevent sedimentation of the solids and capsules. The resulting formulation was a stable suspension of the microcapsules and the Devrinol particles with no noticeable agglomeration.

The foregoing is offered primarily for purposes of illustration. It will be readily apparent to those skilled in the art that substitutions and variations in the materials. proportions and procedures disclosed herein may be made without departing from the spirit and scope of the invention.

What is claimed is:

1. A water-based agricultural formulation comprising a continuous aqueous liquid having suspended therein:

a first dispersed phase comprised of a first herbicide in liquid form encapsulted in a porous shell of inert polymeric diffusion-limiting material which maintains the integrity of the encapsulated phase during storage and application; and a second dispersed phase comprised of a second herbicide with no diffusion-limiting barrier at the surface thereof; and a suspension system to prevent the dispersed phases from agglomerating within themselves and with each other wherein the suspension system includes surfactants, clays, polymers, and other suspension stabilizing materials and wherein the first and second herbicides include thiocarbamates, triazines, amides and dinitroanilines.

2. A formulation in accordance with claim 1 in which said second dispersed phase is comprised of solid particles of said second herbicide.

3. A formulation in accordance with claim 1 in which said second dispersed phase is comprised of liquid droplets comprising said second herbicide in liquid form substantially immiscible with water.

4. A formulation in accordance with claim 1 in which said first herbicide and said second herbicide are the same.

5. A formulation in accordance with claim 1 in which said first herbicide and said second herbicide are different.

6. A formulation in accordance with claim 1 in which said first herbicide is $\alpha, \alpha, \alpha$-trifluoro-2,6-dinitro-N,N-dipropyl-p-toluidine, and said second herbicide is 2-($\alpha$-naphthoxy)N,N-diethylpropionamide.

7. A formulation in accordance with claim 1 in which said first dispersed phase is comprised of a microencapsulated organic solution of $\alpha,\alpha,\alpha$-trifluoro-2,6-dinitro-N,N-dipropyl-p-toluidine, and said second dispersed phase is comprised of solid particles of 2-($\alpha$-naphthoxy)N,N-diethylpropionamide.

8. A formulation in accordance with claim 1 in which said first dispersed phase is comprised of a microencapsulated organic solution of $\alpha,\alpha,\alpha$-trifluoro-2,6-dinitro-N,N-dipropyl-p-toluidine, and said second dispersed phase is comprised of solid particles of 2-($\alpha$-naphthoxy)-N,N-diethylpropionamide, and said suspension system is comprised of a combination of a polyalkylene glycol ether, an ethoxylated alkylaryl ether, an ethoxylated polyarylphenol phosphate, a cresol formaldehyde, a xanthan gum and an attapulgite clay.

* * * * *

UNITED STATES PATENT AND TRADEMARK OFFICE
CERTIFICATE OF CORRECTION

PATENT NO. : 5,049,182

DATED : September 17, 1991

INVENTOR(S) : Herbert B. Scher, Marius Rodson, Jose L. Calvo and Miguel Gimeno

It is certified that error appears in the above-identified patent and that said Letters Patent is hereby corrected as shown below:

On the cover page, under paragraph [56], "References Cited", following the fourth line in column 2, insert the following:

FOREIGN PATENT DOCUMENTS

| | | |
|---|---|---|
| 252897 | 1/1988 | European Pat. Off. |
| 238184 | 9/1987 | European Pat. Off. |
| 017409 | 10/1980 | European Pat. Off. |
| 008207 | 2/1980 | European Pat. Off. |
| 2207440 | 8/1973 | Fed. Rep. of Germany |
| 2052428 | 4/1972 | Fed. Rep. of Germany |
| 2017808 | 10/1971 | Fed. Rep. of Germany |
| 2017356 | 1/1972 | Fed. Rep. of Germany |
| 1960430 | 7/1971 | Fed. Rep. of Germany |

Signed and Sealed this

Twenty-eighth Day of September, 1993

Attest:

BRUCE LEHMAN

*Attesting Officer*  *Commissioner of Patents and Trademarks*